(12) United States Patent
Tockman et al.

(10) Patent No.: US 8,175,724 B2
(45) Date of Patent: May 8, 2012

(54) VASCULAR FIXATION DEVICE

(75) Inventors: Bruce A. Tockman, Scandia, MN (US); Neil M. Becker, Greenfield, MN (US); Cindy L. Sherman, Temecula, CA (US); Kevin M. Phillips, Buffalo, MN (US); Scott A. Stockmoe, Maple Grove, MN (US); Yongxing Zhang, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 550 days.

(21) Appl. No.: 12/337,180

(22) Filed: Dec. 17, 2008

(65) Prior Publication Data

US 2009/0177209 A1 Jul. 9, 2009

Related U.S. Application Data

(63) Continuation-in-part of application No. 11/114,730, filed on Apr. 26, 2005, now Pat. No. 7,477,946.

(51) Int. Cl.
*A61N 1/05* (2006.01)
(52) U.S. Cl. .................................. 607/126; 607/116
(58) Field of Classification Search .................. None
See application file for complete search history.

(56) References Cited

U.S. PATENT DOCUMENTS

| 4,819,661 | A  |    | 4/1989  | Heil, Jr. et al. |          |
|-----------|----|----|---------|------------------|----------|
| 4,827,940 | A  |    | 5/1989  | Mayer et al.     |          |
| 5,071,407 | A  | *  | 12/1991 | Termin et al.    | 604/104  |
| 5,170,802 | A  | *  | 12/1992 | Mehra            | 607/126  |
| 5,221,261 | A  |    | 6/1993  | Termin et al.    |          |
| 5,224,491 | A  |    | 7/1993  | Mehra            |          |
| 5,449,372 | A  |    | 9/1995  | Schmaltz et al.  |          |
| 5,466,255 | A  | *  | 11/1995 | Franchi          | 607/128  |
| 5,514,174 | A  |    | 5/1996  | Heil, Jr. et al. |          |
| 5,531,779 | A  |    | 7/1996  | Dahl et al.      |          |
| 5,632,749 | A  | *  | 5/1997  | Goode et al.     | 606/108  |
| 5,649,906 | A  |    | 7/1997  | Gory et al.      |          |
| 5,674,274 | A  | *  | 10/1997 | Morgan et al.    | 607/123  |
| 5,755,766 | A  | *  | 5/1998  | Chastain et al.  | 607/122  |
| 5,871,531 | A  |    | 2/1999  | Struble          |          |
| 5,902,331 | A  |    | 5/1999  | Bonner et al.    |          |
| 5,951,597 | A  | *  | 9/1999  | Westlund et al.  | 607/126  |
| 5,954,761 | A  |    | 9/1999  | Machek et al.    |          |
| 6,129,750 | A  |    | 10/2000 | Tockman et al.   |          |
| 6,136,021 | A  |    | 10/2000 | Tockman et al.   |          |
| 6,161,029 | A  |    | 12/2000 | Spreigl et al.   |          |
| 6,178,356 | B1 |    | 1/2001  | Chastain et al.  |          |
| 6,397,109 | B1 |    | 5/2002  | Cammilli et al.  |          |
| 6,408,214 | B1 |    | 6/2002  | Williams et al.  |          |
| 6,510,347 | B2 |    | 1/2003  | Borkan           |          |

(Continued)

FOREIGN PATENT DOCUMENTS

EP 0795343 9/1997

(Continued)

*Primary Examiner* — Kennedy Schaetzle
(74) *Attorney, Agent, or Firm* — Faegre Baker Daniels LLP

(57) ABSTRACT

In one embodiment, the present invention provides a cardiac lead device including a fixation mechanism slidably attached to the lead such that when the fixation mechanism is expanded in to contact with a body lumen, the lead may be moved relative to the fixation mechanism if desired. Such lead movement may be limited by complimentary structure on the lead body and the fixation mechanism that prevents the lead from moving unless sufficient force is applied to the lead.

16 Claims, 8 Drawing Sheets

U.S. PATENT DOCUMENTS

| | | | |
|---|---|---|---|
| 6,709,415 B2 | 3/2004 | Navia et al. | |
| 6,711,443 B2 | 3/2004 | Osypka | |
| 6,730,064 B2 | 5/2004 | Ragheb et al. | |
| 6,774,278 B1 | 8/2004 | Ragheb et al. | |
| 6,842,648 B2 | 1/2005 | Partridge et al. | |
| 6,907,285 B2 * | 6/2005 | Denker et al. | 607/5 |
| 7,245,967 B1 * | 7/2007 | Shelchuk | 607/14 |
| 7,519,421 B2 * | 4/2009 | Denker et al. | 607/5 |
| 7,840,266 B2 * | 11/2010 | Libbus et al. | 607/9 |
| 2002/0026228 A1 | 2/2002 | Schauerte et al. | |
| 2002/0045926 A1 | 4/2002 | Heil, Jr. et al. | |
| 2002/0082679 A1 | 6/2002 | Sirhan et al. | |
| 2002/0103522 A1 | 8/2002 | Swoyer et al. | |
| 2003/0065374 A1 | 4/2003 | Honeck | |
| 2003/0083646 A1 | 5/2003 | Sirhan et al. | |
| 2003/0139801 A1 | 7/2003 | Sirhan et al. | |
| 2003/0144727 A1 | 7/2003 | Rosenthal et al. | |
| 2003/0163184 A1 | 8/2003 | Scheiner et al. | |
| 2003/0199961 A1 | 10/2003 | Bjorklund | |
| 2003/0204231 A1 | 10/2003 | Hine et al. | |
| 2003/0220677 A1 | 11/2003 | Doan et al. | |
| 2004/0059404 A1 | 3/2004 | Bjorklund et al. | |
| 2004/0062852 A1 | 4/2004 | Schroeder et al. | |
| 2005/0070985 A1 | 3/2005 | Knapp et al. | |
| 2005/0080472 A1 | 4/2005 | Atkinson | |
| 2005/0131511 A1 | 6/2005 | Westlund | |
| 2006/0009830 A1 * | 1/2006 | Atkinson et al. | 607/126 |

FOREIGN PATENT DOCUMENTS

| | | |
|---|---|---|
| WO | WO 03092799 | 11/2003 |
| WO | WO 2004060478 | 7/2004 |

* cited by examiner

VASCULAR FIXATION DEVICE

CROSS-REFERENCE TO RELATED APPLICATIONS

This application is a continuation-in-part of application Ser. No. 11/114,730 filed Apr. 26, 2005, entitled "Fixation Device for Coronary Venous Lead," now U.S. Pat. No. 7,477,946, which is incorporated by reference herein in its entirety.

TECHNICAL FIELD

The present invention relates to implantable medical devices and, in particular, to fixation of cardiac leads in a patient's vascular system.

BACKGROUND

Cardiac function management systems are used to treat arrhythmias and other abnormal heart conditions. Such systems generally include cardiac leads, which are implanted at a target location suitable for delivering an electrical stimulus therapy to a patient's heart. A cardiac lead typically includes a flexible conductor defining a central channel or lumen, surrounded by an insulating tube or sheath extending from an electrode at the distal end to a connector pin at the proximal end.

Cardiac lead placement may be accomplished by introducing the lead through a major blood vessel and advancing a distal end of the lead to a target location suitable for electrical stimulation of a patient's heart. The target location may be located near or in a patient's heart or at a location adjacent a nerve or nerve bundle. To facilitate cannulation of the vasculature, it is often helpful to first advance a guiding catheter through the desired vascular path. One difficulty with implanting leads in this fashion is that the cardiac lead has a tendency to become dislodged from its desired location during or after lead implantation. For example, when a clinician withdraws the guiding catheter, the lead may dislodge or otherwise reposition. Until tissue in-growth ultimately fixes the lead at the desired site, cardiac leads may also become dislodged by subsequent physiological activity.

SUMMARY

In one embodiment, the present invention provides a cardiac lead system adapted for anchoring in a vessel. In one embodiment, the lead system is adapted for anchoring in a vessel adjacent a nerve. Stimulation of the nerve can result in regulation of cardiac function. The system includes a conductive lead body and an expandable fixation mechanism. The lead body has a proximal end and a distal end and defines a lead lumen extending between the proximal and distal ends. The expandable fixation mechanism has an expanded position adapted to engage an inner surface of the vessel, and is slidably secured to an outer surface of the lead body. The lead body and the fixation mechanism include respective first and second structures that are adapted to contact each other to resist relative longitudinal movement.

The first structure on the lead body may include one or more stops, curves, bends, coils, ridges or other protrusions on the lead body. The second structure may include one or more rings connected to the fixation mechanism and encircling the lead body. In one embodiment, the system further includes a stylet, which may be inserted into the lead body to straighten any curves, bends, or ridges in the lead body, thus reducing the overall diameter of portions of the lead body.

The fixation mechanism may be self-expanding or balloon-expanding. For self-expanding embodiments, the fixation mechanism may be compressed by an outer guide or by a dissolvable material which dissolves upon contacting bodily fluid. In one embodiment, the fixation mechanism is formed similarly to a conventional stent.

In another embodiment, the present invention provides a cardiac lead device including a conductive lead body and an expandable fixation mechanism as reported above, means for compressing the fixation mechanism, and means for resisting the relative movement when the fixation mechanism is secured to the outer surface of the tubular wall of the lead body. The means for compressing the fixation mechanism may include one or more guides through which the lead body and/or fixation mechanism are slidably movable. The means for compressing may also include a dissolvable material as reported above. The means for resisting relative movement may include the first and/or second structure reported above.

The present invention also provides a method for implanting a cardiac lead device in a body lumen. A cardiac lead device as reported herein is guided into the body lumen. A fixation mechanism, which is slidably secured to the lead body, is then deployed from a compressed position to an expanded position to engage the internal wall of the body lumen. The lead can be moved relative to the expanded fixation mechanism in order to reposition the lead. In one embodiment, the lead can be moved along a longitudinal axis of the vessel in which it is deployed. In another embodiment, the lead can be rotated relative to the expanded fixation device. Prior to guiding the lead device, one or more guides may be inserted into the body lumen to facilitate the lead implantation process.

According to some embodiments, the present invention provides a method of implanting a cardiac device in a body lumen adjacent a vagus nerve. In some embodiments, the body lumen is the internal jugular vein. The method includes advancing the cardiac lead device to a target location in a body lumen adjacent the vagus nerve and deploying an expandable fixation mechanism such that the fixation mechanism engages an internal wall of the lumen. The lead can be moved relative to the expanded fixation mechanism in order to reposition the lead. In one embodiment, the lead can be moved along a longitudinal axis of the vessel in which it is deployed. In another embodiment, the lead can be rotated relative to the expanded fixation device.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Figure 1:
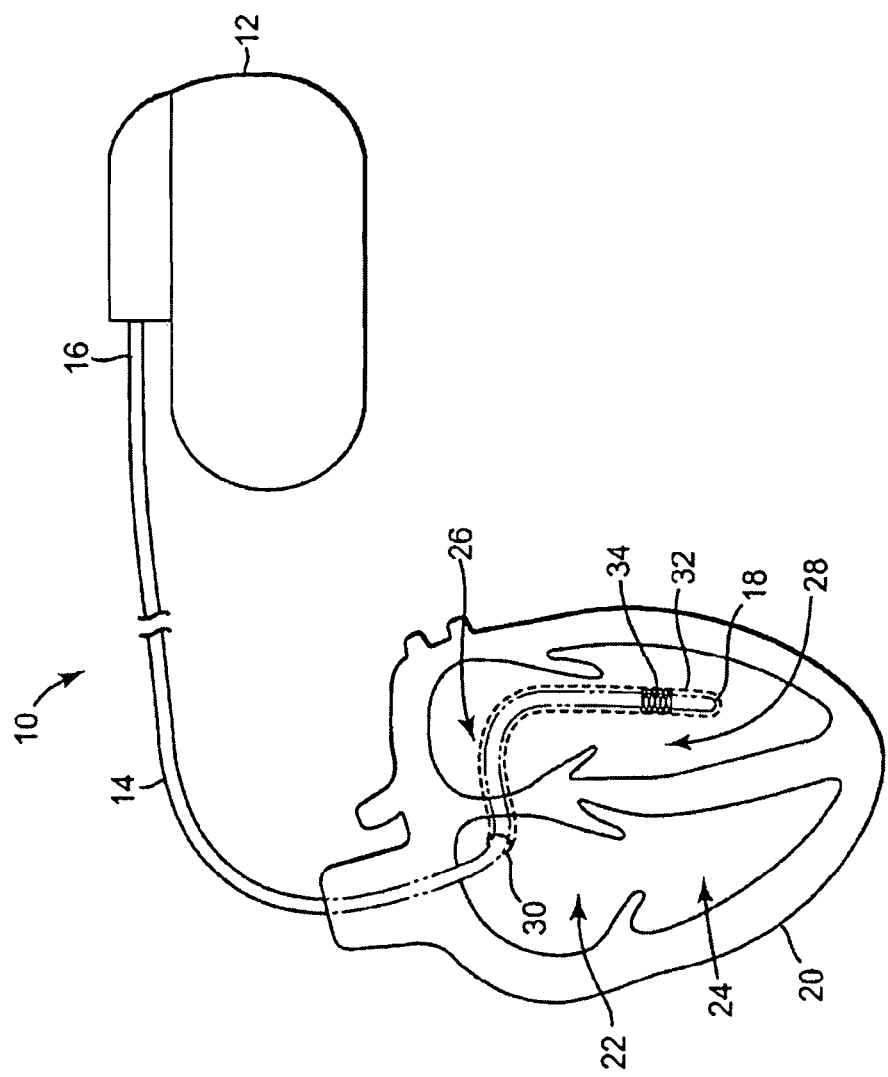
FIG. 1 is a schematic view of a cardiac lead implanted in a cardiac vessel according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

While some of the embodiments described herein generally refer to placement of a lead into a cardiac vessel such as, for example, the great cardiac vein, the various embodiments of the present invention as described below can be practiced at numerous sites within a patient's vasculature system. Any intravascular site that is located in or near a patient's heart or, alternatively, located adjacent to a nerve or muscle that when stimulated with an electrical pulse regulates cardiac function is a potential site for stimulation. In addition to the locations in and near a patient's heart, exemplary stimulation sites include, but are not limited to, the following: the left and right internal jugular veins, the azygous vein, the brachiocephalic (innominate) vein, the subclavian vein, the superior vena cava, and the pulmonary artery. Exemplary nerves to be stimulated in order to affect cardiac function include, but are not limited to, the following: the left and right vagus nerves, the phrenic nerve, the parasympathetic nerves, the sympathetic nerves, and the sacral nerve.

FIG. 1 is a schematic drawing of a cardiac rhythm management device 12 coupled to an intravascular endocardial lead 14 having a proximal end 16 and a distal end 18. Distal portions of the lead 14 are disposed in the vessel located within the patient's heart 20, which includes a right atrium 22, a right ventricle 24, a left atrium 26, and a left ventricle 28. In the embodiment illustrated in FIG. 1, the distal end 18 of lead 14 is transvenously guided into the right atrium 22, through a coronary sinus 30, and into a cardiac vein 31 using techniques known to those of skill in the art. The illustrated disposition of the lead 14 may be used for delivering pacing and/or defibrillation energy through any cardiac vessel, including the cardiac sinus 30, coronary veins or pulmonary artery, to the left ventricle 28 for the treatment of cardiac arrhythmias.

The lead 14, according to the various embodiments discussed below, can also be implanted at other locations within a patient's vasculature. In certain embodiments, distal portions of the lead 14 can be delivered and implanted at a target location within a vessel adjacent a nerve or nerve bundle. The lead 14 is capable of delivering an electrical stimulus pulse across the vessel walls to the adjacent nerve. Stimulation of the nerve or nerve bundle can result in regulation of cardiac function.

Figure 2:
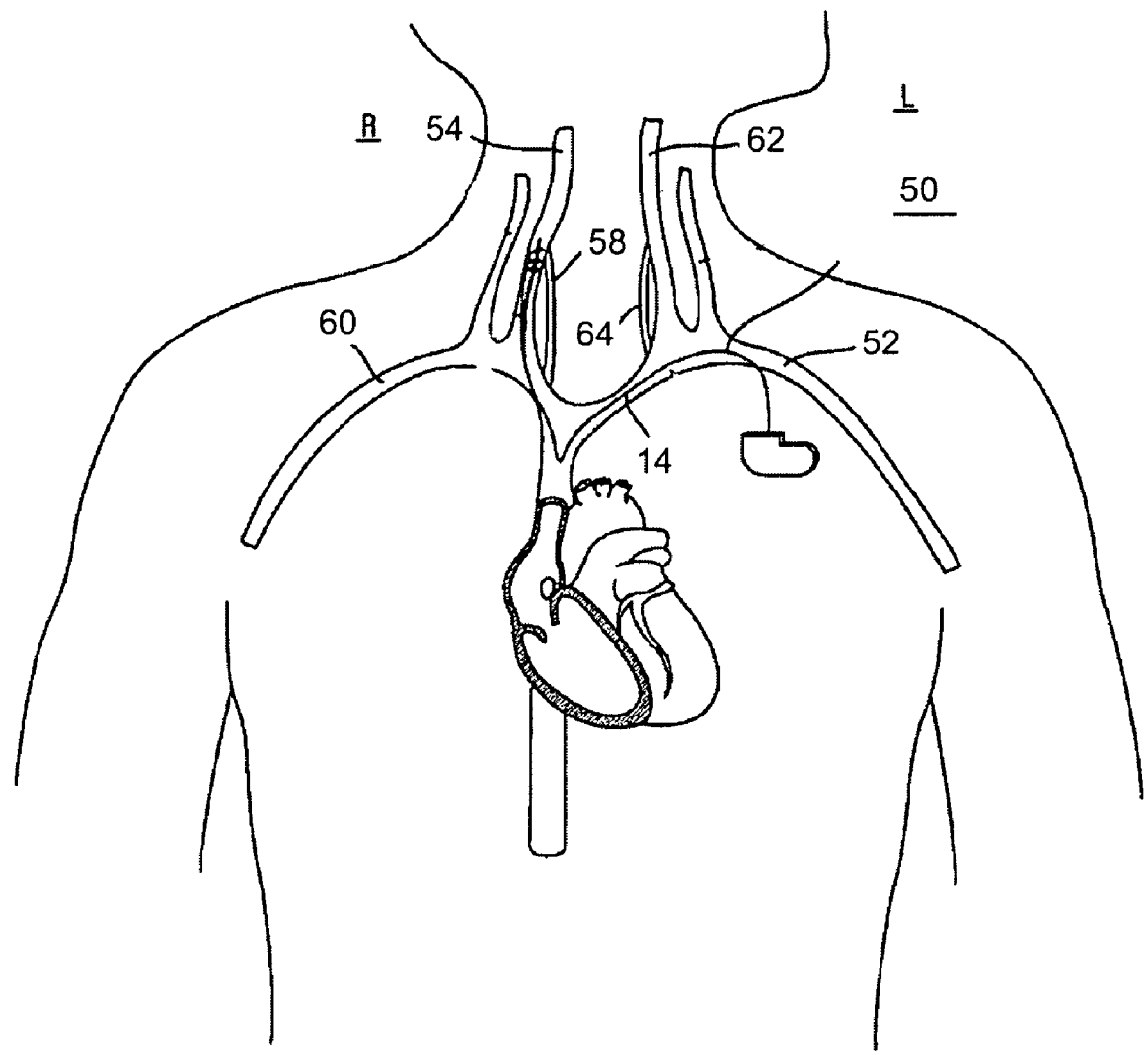
FIG. 2 is a schematic view of a cardiac lead implanted in a patient's internal jugular vein at a location adjacent the vagus nerve according to another embodiment of the present invention.

FIG. 2 shows a perspective view showing a lead 14 deployed at another location within a patient's vasculature system 50. As shown in FIG. 2, the lead 14 is inserted into a patient's vasculature system 50 and advanced through the left subclavian vein 52 and into the right internal jugular vein 54 at a location adjacent the vagus nerve 58. Stimulation of the vagus nerve 58 can result in regulation of cardiac function. In another embodiment, the lead 14 can also be inserted and advanced into an internal jugular vein using a same side approach. For example, the lead 14 may be inserted into the patient's vasculature system 50 through the right subclavian vein 60 and into the right internal jugular vein 54. In yet other embodiments, the lead 14 can be delivered to a target location within a patient's left internal jugular vein 62 to stimulate the right vagus nerve 64. In still other embodiments, the lead 14 can be delivered to a location within a patient's brachiocephalic vein or subclavian vein that is adjacent to the vagus nerve.

Figure 3:
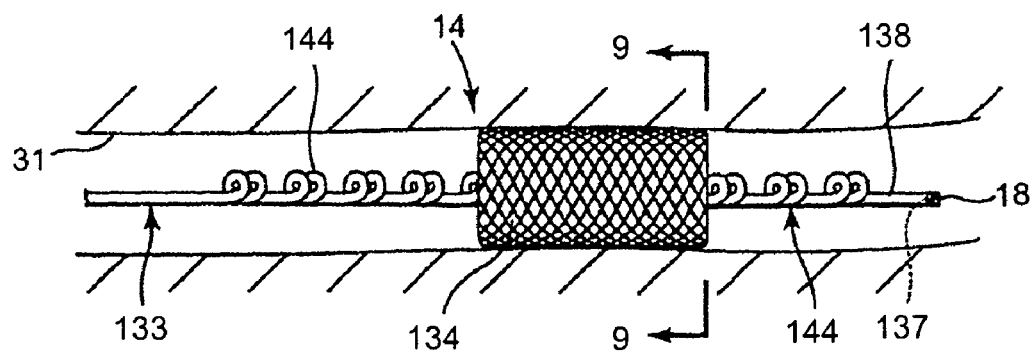
FIG. 3 shows a schematic view of a distal portion of a cardiac lead according to an embodiment of the present invention implanted in a patient's vasculature.
Figure 4:
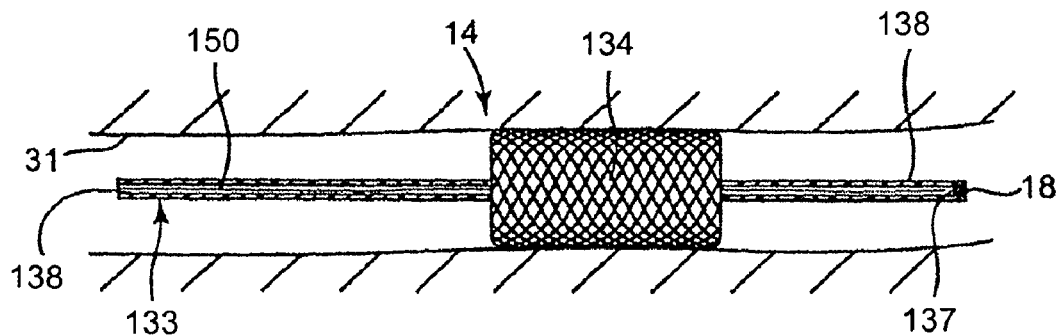
FIG. 4 illustrates the embodiment of FIG. 3 after insertion of a stylet into a lumen of the cardiac lead.
Figure 5:
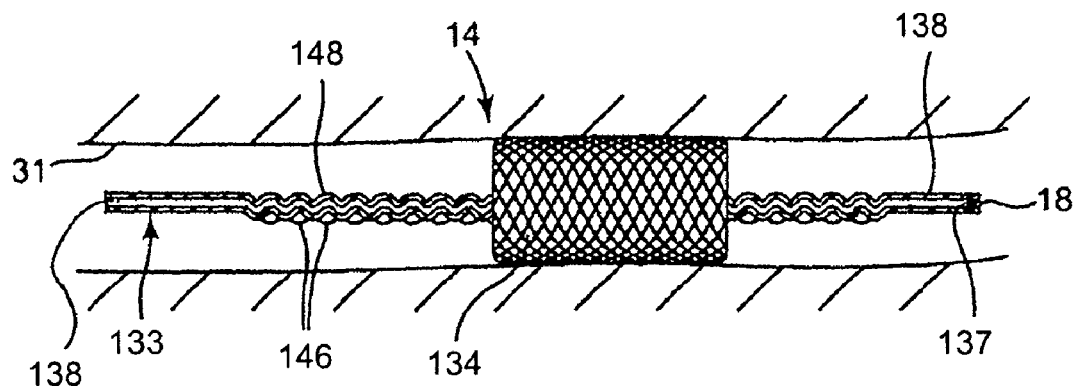
FIG. 5 shows a distal portion of a cardiac lead implanted in a patient's vasculature according to another embodiment of the present invention.
Figure 6:
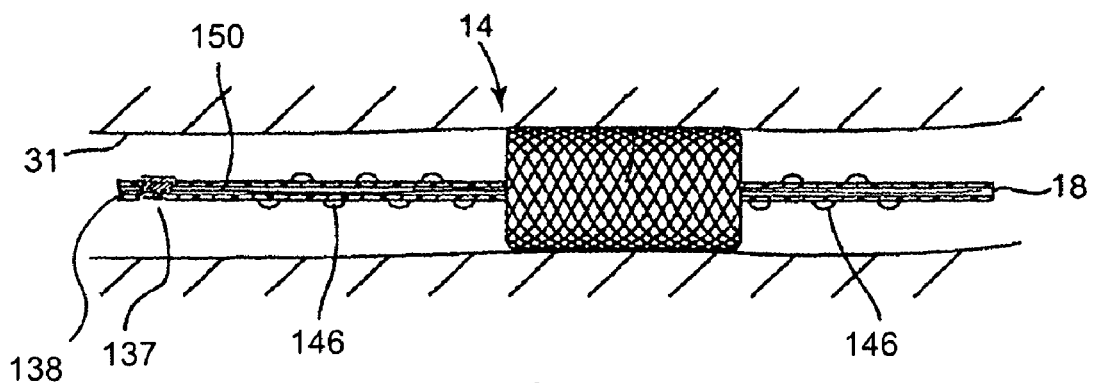
FIG. 6 illustrates the embodiment of FIG. 5 after insertion of a stylet into a lumen of the cardiac lead.
Figure 7A:
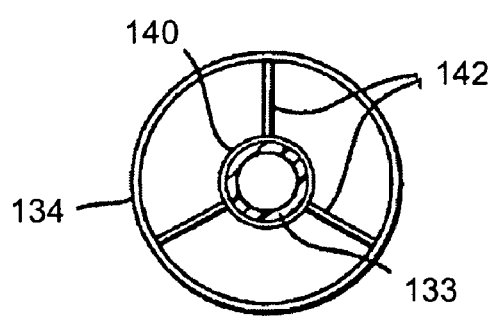
FIGS. 7A-7D show end plan views of multiple embodiments of the present invention.
Figure 7B:
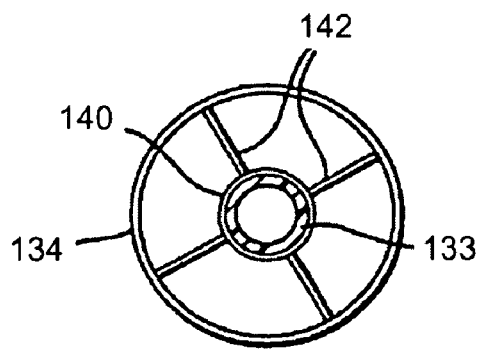
Figure 7C:
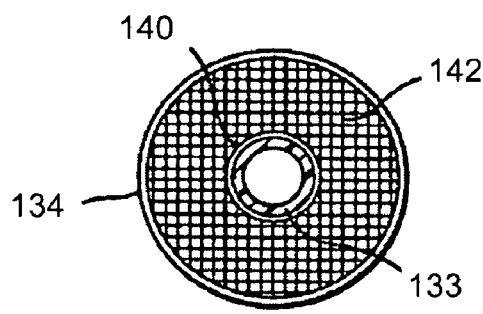
Figure 7D:
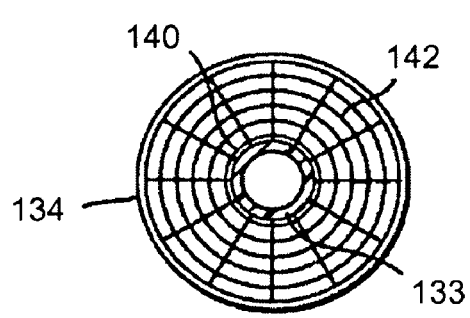

FIGS. 3-6 show cross-sectional views of a vessel 31 into which the cardiac lead 14 has been implanted. The cardiac lead 14 generally includes a lead body 133 and an expandable fixation mechanism 134, which is secured to the lead body 133. The lead body 133 has a proximal end 16 (see FIG. 1) and a distal end 18 and at least one lead lumen 138 extending between the proximal and distal ends 16, 18. The lead body 133 further includes at least one electrode 137 located on the lead body 133 for delivering an electrical pulse. The at least one electrode 137 can be located either proximal or distal to the expandable fixation mechanism 134. In one embodiment, the electrode 137 is located at the distal end 18 of the lead 14 (FIGS. 3-5). In another embodiment, as shown in FIG. 6, the at least one electrode 137 is located on the lead body 133 at a location proximal to the expandable fixation mechanism 134. In certain embodiments, the electrode 137 may be affixed to the wall of vessel 31.

As shown in FIGS. 3-6, the fixation mechanism 134 is configured to contact the vessel 31 when in an expanded position. In certain embodiments, the fixation mechanism 134 is configured in a stent-like form as shown in FIGS. 3-6. Other shapes and configurations may also be suitable for embodiments of the present invention. The fixation mechanism 134 may be formed from conventional stent materials, for example, stainless steel, nitinol, or shape memory alloys or polymers. In a particular embodiment, the fixation mechanism 134 is (or is a modified version of) a Palmaz-Shatz type stent commonly used in vascular intervention procedures. In another embodiment, the fixation mechanism 134 is partially or completely formed from a biodegradable and or dissolvable material that degrades when contacted with body fluid.

The fixation mechanism 134 is slidably secured to the lead body 133 such that the lead body 133 is selectively movable relative to the fixation mechanism 134 along the longitudinal path of the vessel 131 when the fixation mechanism 134 is in the expanded position shown. The lead 14 can be moved relative to the fixation mechanism 134 in either a proximal or a distal direction. In some embodiments, the position of the lead 14 can be adjusted such that one or more electrodes 137 located on the lead body 133 are located either proximal or distal to the fixation mechanism 134. Such selective relative movement is accomplished by providing both the lead body 133 and the fixation mechanism 134 with cooperating or corresponding structures as described in detail below.

The structure on the lead body 133 may be configured to increase a major dimension (e.g. diameter) of the lead body 133 at select locations. Numerous configurations may be employed for the structure on the lead body 133. In the embodiment illustrated in FIG. 3, for example, the lead body 133 includes one or more coiled or looped portions 144, which cooperate with the structure on the fixation mechanism 134 to limit undesired or unintentional longitudinal movement of the lead body 133. In an alternate embodiment, the structure includes a two-dimensional shape such as a sinusoidal shape or a J-bend.

The embodiment illustrated in FIG. 5 includes protrusions 146 secured along a plurality of ridges 148 formed in the lead body 133. The protrusions 146 may be formed as bumps, spheres, ears, rings, or other shapes formed on and extending from the surface of the lead body 133. The protrusions 146 may be formed from silicone or other biocompatible materials and may remain substantially permanently secured to the lead body 133 or may be biodegradable.

The looped portions 144, protrusions 146, or ridges 148 may be positioned anywhere along the length of the lead body 133. In the illustrated embodiments, structure is located both proximal and distal to the fixation mechanism 134 to allow for a range of proximal and distal movement of lead body 133. Other configurations may also be appropriate depending on the specific application of the cardiac lead 14. Furthermore, although FIGS. 3 and 5 show specific structures for limiting movement of the lead body 133, it should be appreciated that a wide range of structures, either individually or in combination, may be used in embodiments of the present invention. The loops 144, protrusions 146, or ridges 148 may be spaced at various adjustment intervals depending on the magnitude of adjustments desired. In one embodiment, for example, these structures are located between about 1 and about 10 millimeters apart, or more preferably between about 2 and about 5 millimeters apart, along the lead body 133.

FIGS. 7A-7D show plan views of the cardiac lead 14 from the perspective of the line 9-9 shown in FIG. 3. As shown in FIGS. 7A-7D, the fixation mechanism 134 includes one or more fixation rings 140 which contact or otherwise interact with structure on the lead body 133 to provide selective movement of the lead body 133. The fixation rings 140 generally encircle the lead body 133, and are generally connected to the outside (i.e. vessel engaging) surface of the fixation mechanism 134 via struts 142. As further shown in FIGS. 7A-7D, the struts 142 may have a variety of configurations. The fixation rings 140 may be formed anywhere along the length of the fixation mechanism 134, but in one embodiment, the fixation rings 140 are disposed on opposing ends of the fixation mechanism 134.

The fixation rings 140 and struts 142 may be formed from a variety of materials, including materials commonly used to form stents. In certain embodiments either or both of the rings 140 and the struts 142 may be formed from an elastic, string, fibrous, or thread-like material. Additionally the fixation rings 140 and the struts 142 may be formed to be biodegradable and/or dissolvable upon contact with bodily fluid, or to remain substantially and permanently in the vessel 31. In one embodiment, the fixation rings 140 and the struts 142 may be formed to biodegrade after a period of time sufficient to allow the lead body to become secured within the vessel 31 by tissue in-growth. For example, the fixation mechanism 134 could be temporarily fixed to the lead body with a resorbable material that would dissolve over a period of weeks or months to allow extraction of the lead at a later date.

As shown in FIGS. 3 and 5, the structures disposed on both the lead body 133 and the fixation mechanism 134 resist longitudinal movement of the lead body 133 relative to the fixation mechanism 134 because the structure on the lead body 133 (i.e. coiled portions 144, protrusions 146 and/or ridges 148) has a major dimension that is greater than the diameter of the fixation rings 140 such that longitudinal movement of the lead body 133 is limited or selectively prevented. In certain embodiments, the structures on the lead body 133 can also prevent rotational movement of the lead body 133 relative to the fixation mechanism 134.

To reposition the lead body 133 according to one embodiment, the major dimension of the lead body 133 in the vicinity of the fixation mechanism 134 may be reduced to a size that is smaller than the diameter of the fixation rings 140, by inserting a stylet or guidewire into the lead lumen 138. For example, FIG. 4 shows the embodiment of FIG. 3 after inserting a stylet or guidewire 150 such that the coiled portions 144 are straightened. FIG. 6 shows the embodiment of FIG. 5 after inserting a stylet or guidewire 150 such that the ridges 148 are straightened. In both cases, the lead body 133 becomes movable relative to the fixation mechanism 134 along the longitudinal path of the vessel 31. In certain embodiments, the lead 14 also becomes rotatable relative to the fixation mechanism 134. Rotation of the lead 14 allows the at least one electrode 137 to be oriented towards the target stimulation site. After repositioning the lead body 132, the stylet or guidewire 150 may be removed such that the structure returns to the shape shown in FIGS. 3 and 5, which again limits longitudinal and/or rotational movement of the lead 133 with respect to the fixation mechanism 134. According to another embodiment, instead of changing the major diameter of the lead, the interacting structures on the lead body 133 and the fixation rings 140 have sufficient flexibility to allow the structures to pass through the rings upon application of a sufficient force at the proximal end 16 of the lead body 133.

Figure 8:
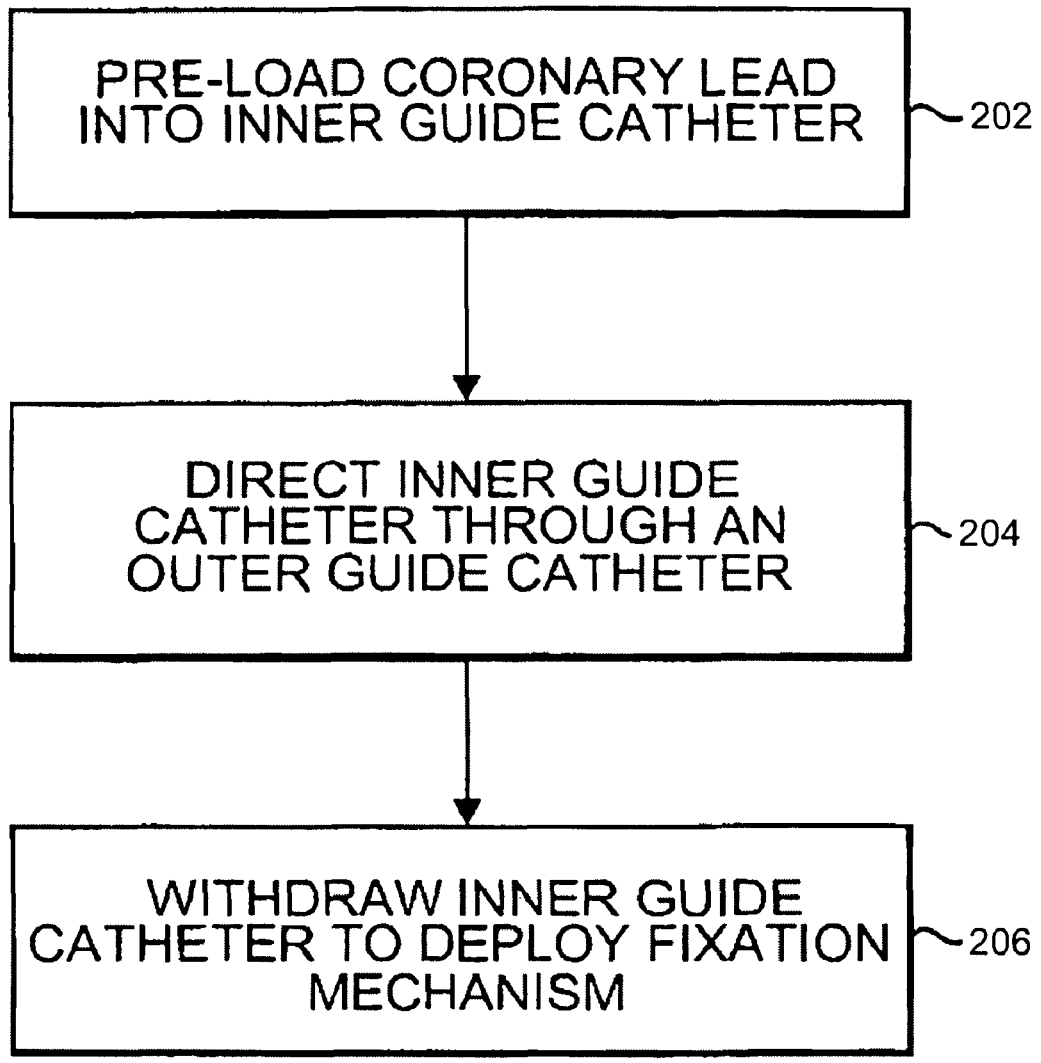
FIG. 8 is a flowchart illustrating a method for implanting a cardiac lead according to one embodiment of the present invention.
Figure 9:
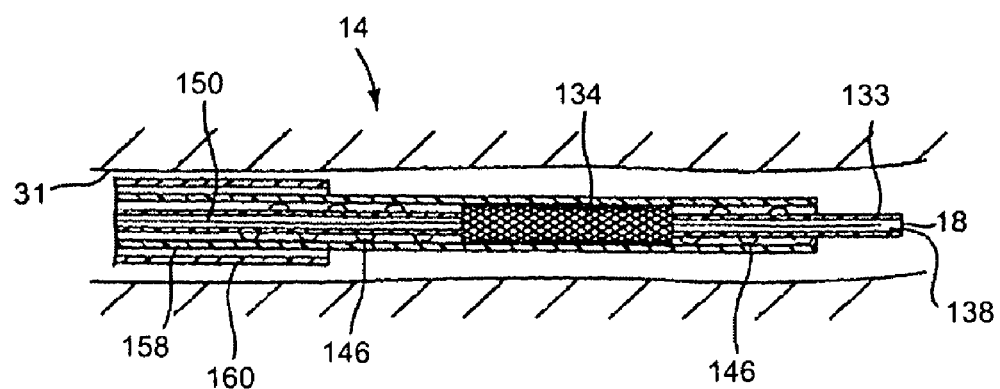
FIG. 9 shows a cardiac lead being implanted according to the method described in FIG. 8.
Figure 10:
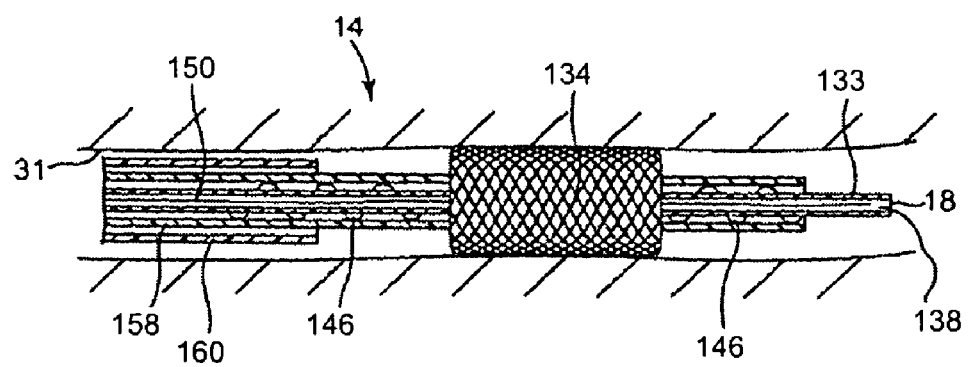
FIG. 10 is a flowchart describing an alternate method for implanting a cardiac lead according to one embodiment of the present invention.

FIGS. 9-10 depict a method of implanting the cardiac lead 14 according to an embodiment of the present invention. FIG. 8 is a flow-chart showing a method of implanting the cardiac lead 14 according to one embodiment of the present invention. The cardiac lead 14 is pre-loaded into an inner guide catheter 158 such that the fixation mechanism 134 is in a compressed position (block 202). The inner guide catheter 158 is then directed through the patient's vasculature, optionally through an outside guide catheter or sheath 160, to a desired location in the patient's vasculature (block 204) as shown in FIG. 8. The inner guide catheter 158 is then withdrawn such that the fixation mechanism 134 deploys to an expanded position (block 206) shown in FIGS. 3-6. The fixation mechanism 134, in this embodiment, may expand by, for example, self-expansion or balloon expansion. In one embodiment, after the fixation mechanism 134 is expanded and secured to the wall of the vessel 31, the longitudinal position of the lead body 133 may be adjusted. In yet another embodiment, the lead body 133 can be rotated relative to the fixation mechanism 134. The stylet or guidewire 150 is then removed, which allows the lead 133 to resume its default shape (see, for example, FIGS. 3 and 5) having an increased major diameter, which, in turn, limits or resists further longitudinal movement of the lead body 133.

In a variation of the method described in FIGS. 8-9, the fixation mechanism 134 may be fixed to the lead body 133 in a compressed state with a dissolvable material such as manitol. The lead 14 is inserted through an inner guide catheter 158 until positioned as desired. The lead 14 could then be advanced out of the inner guide catheter 158 to the desired position, which would also expose the dissolvable material to blood. After a short period of time the dissolvable material would dissolve, allowing the fixation mechanism 134 to expand and contact the vessel wall.

Figure 11:
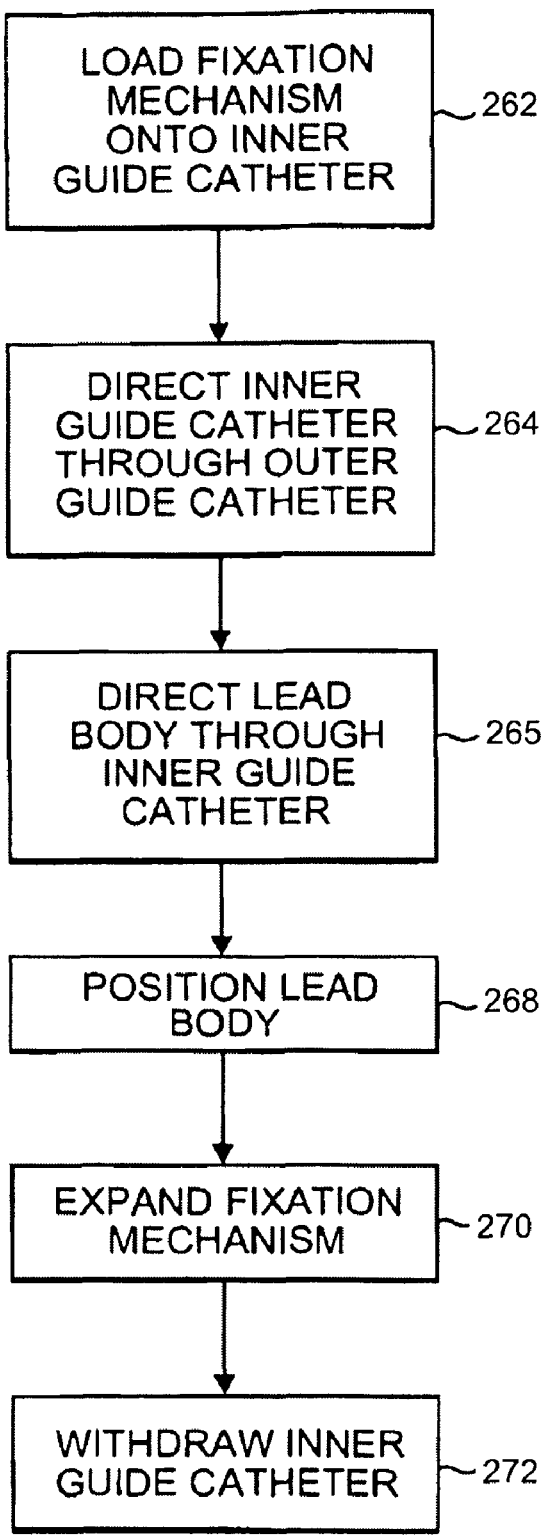
FIG. 11 illustrates a cardiac lead implanted according to the method illustrated in FIG. 10.

FIGS. 10-11 depict a method of implanting the cardiac lead 14 according to another embodiment of the present invention. FIG. 11 is a flow-chart summarizing a method of implanting the cardiac lead 14 according to an embodiment of the present invention, in which the fixation mechanism 134 is initially positioned on an outer surface of the inner guide catheter 158 (block 262) with an optional inflation balloon 159 disposed between the fixation mechanism 134 and the inner guide catheter 158. The inner guide catheter 158 is then directed through an outside guide catheter 160 and into a desired location in a patient's vasculature (block 264). The lead body 133 is then directed through the inner guide catheter 158 (block 266) until the distal end 18 of the lead body 133 extends past the distal end of the inner guide catheter 158 and into a desired location (block 266) as shown in FIG. 10. The fixation mechanism 134 is then expanded via self-expansion or by inflating the optional balloon 159 in a conventional manner (block 270). The inner guide catheter 158 is then withdrawn such that the fixation rings 140 encircle the lead body 133 as shown in FIGS. 3-6 (block 272). After the fixation mechanism 134 is expanded and secured to the wall of the vessel 31, the longitudinal position of the lead body 133 may be adjusted. In a further embodiment, the lead body 133 can also be rotated relative to the fixation mechanism. The stylet or guidewire 150 is then removed, which allows the lead body 133 to resume its default shape (see, for example, FIGS. 3 and 4) having an increased major diameter, which, in turn, limits or resists further longitudinal and/or rotational movement of the lead body 133.

In a variation to the method shown in FIGS. 10-11 and described above, the fixation mechanism 134 is disposed on the inner guide catheter 158 and is pre-loaded into the outside guide catheter 160. After positioning the inner and outer guide catheters 158, 160 and the lead body 133 as described above, a tube or other structure (not shown) may be directed between the inner and outer guide catheters 158, 160 to deploy the fixation mechanism 134 into an expanded position shown in FIGS. 3-6.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

We claim:

1. A method for implanting a cardiac lead device in a body lumen comprising:
    initially implanting an outer guide into the body lumen, the outer guide having a proximal end and a distal end and including a tubular wall defining a lumen extending between the proximal and distal ends;
    guiding an inner guide through the outer guide;
    guiding the cardiac lead device into the body lumen through the inner guide, the device including a conductive lead body having a proximal end and a distal end, the lead body defining at least one lead lumen extending between the proximal and distal ends, the lead body including a tubular wall; and
    deploying an expandable fixation mechanism from a compressed position to an expanded position such that the fixation mechanism engages an internal wall of the body lumen with the lead body extending through the expandable fixation mechanism, the fixation mechanism being secured to an outer surface of the tubular wall of the lead body to provide selective relative movement between the fixation mechanism and the lead body; and
    moving the lead body relative to the expanded fixation mechanism.

2. The method of claim 1 wherein the step of moving the lead body includes the step of inserting a guidewire or stylet into the lead lumen prior to moving the lead body relative to the expanded fixation mechanism.

3. The method of claim 1, wherein the fixation mechanism is disposed on an outer surface of the tubular wall of the inner guide, and the deploying step comprises positioning the fixation mechanism distally of the distal end of the outer guide, expanding the fixation mechanism, and removing the outer and inner guides such that the fixation mechanism is slidably secure to the lead body.

4. The method of claim 1, wherein the deploying step includes moving the fixation mechanism distally of the distal end of the outer guide and self-expanding the fixation mechanism.

5. The method of claim 1, wherein the moving step includes inserting a tube between the outer guide and the inner guide and forcing the fixation mechanism distally of the distal end of the outer guide.

6. The method of claim 1, wherein the fixation mechanism is held in the compressed position by a dissolvable material, and the deploying step includes contacting the dissolvable material with bodily fluid to expand the fixation mechanism.

7. A method for implanting a cardiac lead device comprising:
    advancing the cardiac lead device to a target location within a vessel adjacent a vagus nerve, the vessel being any one of a right internal jugular vein, a left internal jugular vein, a brachiocephalic vein, or a superior vena cava, the device including a conductive lead body having a proximal end and a distal end, the lead body defining at least one lead lumen extending between the proximal and distal ends, at least one electrode located on the lead body, and an expandable fixation mechanism secured to an outer surface of the lead body;
    deploying the expandable fixation mechanism from a compressed configuration to an expanded configuration such that the fixation mechanism engages an internal wall of the vessel to provide selective relative movement between the fixation mechanism and the lead body along a longitudinal axis of the lead body; and
    moving the lead body relative to the expanded fixation mechanism to adjust a position of the cardiac lead device in the vessel.

8. The method of claim 7, wherein the step of moving the lead body relative to the expanded fixation mechanism comprises moving the lead body along a longitudinal axis of the vessel.

9. The method of claim 7, wherein the step of moving the lead body relative to the expanded fixation mechanism comprises rotating the lead body relative to the fixation mechanism.

10. The method of claim 7, further comprising reducing a major dimension of the lead body.

11. The method of claim 7, further comprising inserting and advancing the cardiac lead device through a subclavian vein.

12. The method according to claim 7, wherein the vessel adjacent the vagus nerve is a right or left internal jugular vein.

13. The method according to claim 7, wherein the step of moving the lead relative to the expanded fixation mechanism comprises inserting a guidewire or stylet into the lead lumen prior to moving the lead.

14. The method according to claim 7, wherein the step of moving the lead body comprises moving the lead body relative to the fixation mechanism such that the at least one electrode is located proximal to the fixation mechanism.

15. The method according to claim 7, wherein the step of moving the lead body comprises moving the lead body relative to the fixation mechanism such that the at least one electrode is located distal to the fixation mechanism.

16. The method according to claim 7, further comprising the steps of:

delivering a guide catheter to the target location within the vessel adjacent the vagus nerve, the guide catheter comprising a proximal and a distal end and including tubular wall defining a lumen extending between the proximal and distal ends;

guiding the cardiac lead device through the guide catheter; and advancing the fixation mechanism beyond a distal end of the guide catheter to transition the fixation mechanism from the compressed configuration to the expanded configuration.

* * * * *